United States Patent [19]

Prosen

[11] 4,124,382
[45] Nov. 7, 1978

[54] DENTAL ALLOY FOR USE IN THE ADHESION OF PORCELAIN

[75] Inventor: Emil M. Prosen, Bala-Cynwyd, Pa.

[73] Assignee: Neoloy Products, Inc., Posen, Ill.

[21] Appl. No.: 822,146

[22] Filed: Aug. 5, 1977

[51] Int. Cl.$^2$ ................................................ C22C 5/02
[52] U.S. Cl. .................................................. 75/172 R
[58] Field of Search ............. 75/172 R; 65/154; 32/8; 428/434; 156/89

[56] References Cited

U.S. PATENT DOCUMENTS

| | | | |
|---|---|---|---|
| 1,797,236 | 3/1931 | Klausmann et al. | 75/172 R |
| 3,052,982 | 9/1962 | Weinstein et al. | 32/8 |
| 3,961,420 | 6/1976 | Tuccillo | 32/8 |

FOREIGN PATENT DOCUMENTS

| | | | |
|---|---|---|---|
| 13,032 | 7/1956 | Fed. Rep. of Germany | 75/172 R |
| 2,043,492 | 1/1972 | Fed. Rep. of Germany | 75/172 R |

*Primary Examiner*—L. Dewayne Rutledge
*Assistant Examiner*—Peter K. Skiff
*Attorney, Agent, or Firm*—Cooper, Dunham, Clark, Griffin & Moran

[57] ABSTRACT

The present invention provides a precious metal alloy consisting essentially of palladium and up to 25% tin, up to 2% iron, up to 1% aluminium, and up to 1½% boron. In its preferred form the tin content is approximately 15%, the iron content is approximately 0.83%, the aluminum content is approximately 0.5%, and the boron content is approximately 0.17%. The alloy has a melting point of approximately 2650° F. It is especially adapted for low-fusing porcelain application, and well suited for dental use. It is an economy precious metal alloy as it contains no gold and no platinum. Between 1% and 5% of ruthenium may be added as a hardening element. 3% of ruthenium has been found to be ideal.

6 Claims, No Drawings

DENTAL ALLOY FOR USE IN THE ADHESION OF PORCELAIN

The present invention relates to a precious metal alloy especially adapted for use in the dental field for the preparation of caps, crowns, inlays, partial appliances and other dental prostheses to which it is desired to apply a porcelain or other like ceramic surface. In its broadest aspects the alloy of the present invention not only has specific use in the dental field, but has general use in the field of jewelry and like areas. The most important advantage of the alloy of the present invention, however, is in the dental field in that it provides an alloy to which a low-fusing porcelain can be adhered by fusion, with none of the disadvantages of heretofore known alloys.

It is also an economy alloy in that it does not contain any of the higher priced metals such as gold and platinum.

BACKGROUND OF THE INVENTION

In the dental field one of the most sought after alloys is one to which porcelain can be applied by fusion and which will have complete adhesion throughout the temperature range and other conditions to which the alloy and porcelain will be subjected during processing and use.

Among the many well recognized problems in applying low-fusing porcelain to a dental alloy to provide exterior porcelain surfaces thereon is that the coefficient of expansion of the alloy and the porcelain should be completely matched and compatable so that on cooling the porcelain will not check, crack or separate from the metal alloy.

Also, with precious metal alloys such as alloys of yellow gold, platinum and palladium in fractional percentages it has not been possible to obtain a true bond between the alloy and the porcelain. Hence various alternatives have been suggested for adding to a precious metal alloy other metal elements which at porcelain fusing temperatures would provide on the surface of such alloy bonding oxides.

Among the metals proposed to be added to provide such bonding oxides were copper, cobalt and silver. It has been found, however, that the oxides of cooper, cobalt and silver are undesirable for dental purposes from the standpoint of esthetics for the reasons that copper oxide turns porcelain green; cobalt oxide turns porcelain blue; and silver oxide turns porcelain yellow.

Another disadvantage of yellow gold precious metal alloy from the standpoint of application of a low-fusing porcelain is that yellow gold melts at 1940° F. and low-fusing porcelain fuses at 1800° F. As a consequence the temperature differential between the yellow gold and the fusing porcelain was too close and the yellow gold was unable to maintain its rigidity during the fusing operation.

In order to strengthen yellow gold and to improve its rigidity for the purpose of fusing porcelain thereto, it has heretofore been proposed to add platinum and palladium to provide a precious metal alloy. In order to maintain the yellow color of gold, however, it has been found that the white metals (platinum and palladium) should not exceed 10% of the alloy composition.

In view of the high cost of gold and its high specific gravity, which approximates 19, efforts have been made to employ palladium as a substitute for yellow gold.

Even though palladium has the white color, it was thought desirable to employ palladium in dental alloys because of the other physical and workability characteristics of such alloy. Also, as a substitute for yellow gold it was found that palladium could be combined with silver, nickel and other elements to provide an alloy suitable for porcelain application which would have the high temperature melting point necessary and would also have the rigidity of an alloy structure necessary for porcelain application.

Among the prior art patents generally relating to the subject matter of this invention are:

U.S. Pat. No. 3,819,366 in the name of Michel Katz and entitled "Dental Alloy," wherein the precious alloy for use in dental frames on which ceramic coverings or acrylic coverings are formed consists of 8–76 weight percent palladium and 0.2–18 weight percent indium, 0–15 weight percent zinc, and other trace metals in amounts no greater than 1¾ weight percent.

Schaffer U.S. Pat. No. 3,928,913, entitled "Palladium Alloy for Ceramic Bonding" discloses a dental casting alloy consisting essentially of 40–60 percent of a precious metal component selected from the group consisting of palladium and mixtures of palladium and platinum wherein the platinum is in the amount of up to 12 percent of the alloy but not in excess of 25 percent of the palladium content; 20–59 percent of a non-precious metal component selected from the group consisting of 20–50 percent cobalt and mixtures of 20–50 percent cobalt and up to 25 percent nickel wherein the nickel content does not exceed the cobalt content; and a modifier selected from the group consisting of 1–8 percent indium, 1–3 percent tin and 1–8 percent of mixtures of tin and indium wherein the tin does not exceed 3 percent.

U.S. Pat. No. 3,929,474, dated Dec. 30, 1975 for "Tarnish Resistant Silver Based Dental Casting Alloy Capable of Bonding to Porcelain" in the name of Clyde E. Ingersoll, discloses and claims an alloy to which porcelain may be directly fused, — the alloy composition comprising: 35–60% Pd, at least about 0.5–7% of one member of the group consisting of Cr, Fe, In and Sn and from about 0 to 5% of the group consisting of Si, Ni, Co, Ta, and Ti, and the rest Ag.

For completeness of disclosure it should be noted that Schaffer U.S. Pat. No. 3,928,913 also mentions molybdenum in the amount of 2–8 percent as a desirable additive and that nickel in the amount of 10–20 percent desirably comprises a portion of the non-precious metal component.

SUMMARY OF THE INVENTION

In my experimental work looking toward a precious metal dental alloy which would meet all of the pre-existing requirements for adhesion of low-fusing porcelain, I decided to concentrate on palladium as a substitute for yellow gold and platinum. In my early experiments with palladium I used boron as part of the alloy and found that with boron in small percentages such as 2%, the alloy of palladium and boron melted at about 2600° F. and formed a very desirable alloy. I also found, however, that when the alloy thus prepared was brought up to a temperature of 1800° F. for adhesion of low-fusing porcelain the alloy became very brittle and had no stability. Thus as part of my experimentation I have found that palladium when alloyed with boron in small percentages such as 2% would melt at 2600° F. to form a very desirable alloy, — but does not lend itself to the application of low-fusing porcelain when it is subsequently brought to the temperature of 1800° F. for adhesion of such low-fusing porcelain for the reason that the alloy becomes very brittle at elevated temperatures and has no stability.

I then embarked of further experimentation in order to eliminate, if possible, the undesirable brittleness of the palladium-boron alloy when fusing with porcelain at 1800° F. By repeated experimentation and using almost every metallic element in the periodic table, I finally discovered that with the addition of up to 25% tin, up to 2% iron, and up to 1% aluminum, and by using no more than 1½% boron, I obtained an alloy which during the fusion of porcelain became completely stable, an in final form exhibited complete resistance to separation of the porcelain from the alloy under the impact of the most severe tests. I also found that with the application of heavy blows on impact tests the porcelain did crack and chip away, but the porcelain still was retained on the surface of the alloy because the adhesion of the porcelain to the alloy was stronger than the porcelain itself. Finally, I found that in order to remove all of the porcelain from the alloy it was necessary either to grind it off or to dissolve it in hydrofluoric acid. It will be recognized from the foregoing that the alloy and the porcelain have coefficients of expansion which are compatible with each other.

It will be understood that in dental restorations the bulk of the restoration should be minimal for the patient's comfort and cosmetic appearance. Yet, at the same time, it must have the rigidity and strength to perform the functions of mastication without disturbing the porcelain finish. It has been found that with dental restorations utilizing the present alloy, lightweight, non-bulky restorations can be made which have all of the necessary rigidity and strength to withstand normal mastication and to support without cracking or checking effect on the porcelain adhered thereto, — the porcelain not being required to withstand the strains and stresses of mastication but on the contrary the latter being fully handled by the alloy forming the underlying structure of the restoration.

In my experiments with the use of boron I have found that with the small percentage of boron set forth it not only acts as a flux and a non-oxidizing element, but it also has the observed advantage that when alloyed with palladium under temperatures of 2650° F. it "sweats" and gravitates to the surface to prevent any oxidation. In this condition boron lends itself completely to a close affinity to the porcelain because it becomes homogeneous with the porcelain fused thereto.

To summarize my experimentation results I would say that a precious metal alloy consisting chiefly of palladium and containing about 15% tin, 0.83% iron, 0.5% aluminum and 0.17% boron constitutes a dental alloy which has a melting point of approximately 2650° F. which is capable of being fused to low-fusing porcelain at about 1800° F. and which has the requisite rigidity to prevent checking of the porcelain under fusing and other use conditions to which dental restoration is subjected.

Also, the precious metal alloy of the present invention is an ecomony alloy which can be produced at relatively low cost compared with alloys containing gold and platinum which are high priced metals.

From the foregoing detailed description of the present invention it will be understood that in its broadest aspect the invention provides an alloy of special use in the dental field which consists primarily of palladium and up to 25% tin, up to 2% iron, up to 1% aluminum and up to 1½% boron. This alloy has a melting point of approximately 2650° F. and is usable as a dental alloy either with or without the application of fusing porcelain. It will also be understood that the preferred formulation for the present alloy is:

Palladium: 84%
Tin: 15%
Iron: 0.83%
Aluminum: 0.5%
Boron: 0.17%

Finally, it has been found that control of the desired rigidity or hardness of the cast alloy may be obtained by the addition of 1% to 5% of ruthenium. 5% of ruthenium makes the cast alloy very hard. 3% is ideal and imparts the preferred hardness or rigidity to the cast alloy prior to the application of porcelain.

What is claim is:

1. A precious dental metal alloy particularly adapted to have porcelain and like ceramics fused thereto consisting essentially of palladium, an effective amount up to 25% tin, a small percentage of each of the following elements up to 2% iron, up to 1% aluminum, and up to 1½% boron and the balance palladium.

2. A precious dental metal alloy according to claim 1, wherein the tin content is approximately 15%, the iron content is approximately 0.83%, the aluminum content is approximately 0.5%, and the boron content is approximately 0.17%.

3. A precious dental metal alloy according to claim 2, having a melting point of approximately 2650° F., said alloy and porcelain having coefficients of expansion which are compatible with each other.

4. A precious dental metal alloy according to claim 1, containing in addition thereto between 1% and 5% of ruthenium.

5. A precious dental metal alloy according to claim 2, containing in addition thereto approximately 3% ruthenium.

6. A precious dental metal alloy according to claim 2, containing in addition thereto approximately 3% ruthenium, said alloy having a melting point of approximately 2650° F., and said alloy and porcelain having coefficients of expansion which are compatible with each other.

* * * * *

UNITED STATES PATENT AND TRADEMARK OFFICE
CERTIFICATE OF CORRECTION

PATENT NO. : 4,124,382
DATED : November 7, 1978
INVENTOR(S) : EMIL M. PROSEN

It is certified that error appears in the above-identified patent and that said Letters Patent are hereby corrected as shown below:

Column 1, line 46, change "cooper" to -- copper --;
line 51, after "of" insert -- a --

Column 3, line 6, change "of" to -- on --;
line 15, change "an" to -- and --

Column 4, line 50, after "3%" insert -- of --

Signed and Sealed this

Twenty-sixth Day of February 1980

[SEAL]

Attest:

SIDNEY A. DIAMOND

Attesting Officer

Commissioner of Patents and Trademarks